United States Patent [19]

Gessman

[11] 4,102,332

[45] Jul. 25, 1978

[54] REMOTE, TELEPHONIC CARDIAC RESUSCITATION DEVICE

[76] Inventor: Lawrence J. Gessman, 21 Sabine Ave., Narberth, Pa. 19072

[21] Appl. No.: 797,754

[22] Filed: May 17, 1977

[51] Int. Cl.² ............................................. A61N 1/36
[52] U.S. Cl. .......................... 128/2.1 A; 178/218 A; 128/419 D
[58] Field of Search ................... 128/2.06 A, 2.06 E, 128/2.06 R, 2.1 A, 218 A, 218 R, 419 D

[56] References Cited

U.S. PATENT DOCUMENTS

| | | | |
|---|---|---|---|
| 3,144,019 | 8/1964 | Haber | 128/2.06 A |
| 3,179,890 | 4/1965 | Warner | 128/2.1 R |
| 3,212,496 | 10/1965 | Preston | 128/2.06 R |
| 3,465,103 | 9/1969 | Lynch | 128/2.1 A |
| 3,703,900 | 11/1972 | Nagel | 128/419 D |
| 3,724,455 | 4/1973 | Unger | 128/2.06 A |
| 3,841,328 | 10/1974 | Jensen | 128/218 A |
| 3,910,260 | 10/1975 | Sarnoff et al. | 128/2.1 A |
| 3,920,005 | 11/1975 | Gombrica | 128/2.06 R |
| 3,923,060 | 12/1975 | Ellinwood, Jr. | 128/2.06 A |
| 3,938,507 | 2/1976 | Sarnoff et al. | 128/2.1 A |

FOREIGN PATENT DOCUMENTS

| | | | |
|---|---|---|---|
| 1,202,427 | 7/1959 | France | 128/2.06 R |
| 1,467,344 | 3/1977 | United Kingdom | 128/419 D |

*Primary Examiner*—William E. Kamm
*Attorney, Agent, or Firm*—Benasutti Associates, Ltd.

[57] ABSTRACT

The present invention comprises a simple low cost remote cardiac resuscitation device, the patient's portion of which is particularly adapted to be fitted into a "false bottom" briefcase or other hand carried article until needed. The device is compact, easily applied by the patient at the onset of a symptomatic attack, and will place at the command of an attending cardiologist all of the information which is required and the ability to provide primary resuscitative care to that patient via remote control pending the arrival of trained medical personnel.

24 Claims, 5 Drawing Figures

REMOTE, TELEPHONIC CARDIAC RESUSCITATION DEVICE

BACKGROUND OF THE INVENTION

The present invention generally relates to cardiac resuscitation devices which may be worn or carried by patients prior to the onset of any acute symptoms which may lead to a cardiac arrhythmia, etc. In particular, the present invention relates to the field of such apparatus which are intended to be carried by the patient either at all times or as often as possible, which devices are adapted through a telephonic interface to transmit information to a cardiologist begining at the onset of cardiac symptoms.

Of the approximately 500,000 coronary deaths each year in the USA, 50–70% are sudden deaths (defined as death within 24 hours of onset of acute symptoms) outside the hospital. The cause of death in most of these patients was a potentially treatable cardiac arrest due to a ventricular arrythmia. The coronary care unit experience has almost eliminated arrythmias as a cause of death once the patient comes within its confines because many arrythmias are prevented and the ones that occur are rapidly treated with cardiopulmonary resuscitation and defibrillation. Unfortunately, there are technical and logistical problems in preventing or treating a cardiac arrest rapidly in victims outside the hospital setting because of the speed of their occurrence. A Maryland study found that 40% of cardiac arrests occurred within 15 minutes of the onset of the patient's symptoms, 60% occurring within 1 hour, and 80% of arrests occurring within 4 hours of symptoms. 63% of these cardiac arrests occurred at the victims home, 5% at work, and the remainder at miscellaneous locations. Considering that the mean time between onset of acute coronary symptoms and the patients arrival in the hospital emergency room has been estimated at 3.5 hours in the USA, most patients experience a cardiac arrest prior to arrival at a facility where it can be treated. This total time can be broken up into a decision time-the period between acute onset of symptoms to calling for an ambulance or deciding to seek medical help — and a transportation time — the time it takes an ambulance suitably equipped with resuscitation equipment to arrive at the patient's location once called, or an unequipped ambulance to arrive at the patient's location and transport the victim to a suitably equipped hospital emergency room. The decision time has been estimated at 200 minutes and the transportation time at 30–40 minutes in a review of the reported literature. Currently, some municipalities have organized fast reaction rescue teams which have reduced the transportation time to as low as 5 to 15 minutes. This is particularly true where the financial resources are available to utilize mobile coronary care units manned by M.D.'s and/or paramedics or rescue squads capable of defibrillating victims on the "go ahead" from hospital based physicians receiving the patients "EKG" via telemetry. Unfortunately, this approach is expensive and the speed of arrival, and therefore, survival results are highly dependent upon geographic location, traffic conditions, population density and the number of mobile units in the system. Moreover, this approach does not reduce the average 200 minute patient delay in seeking medical aid unless combined with a population education program aimed at teaching the significance of the coronary symptoms, the urgency in seeking medical aid rapidly, and the overcoming of patient denial of the importance of chest pain because of fear of myocardial infarction and its consequences and the skills of cardiopulmonary resuscitation. For the reasons discussed above, educating patients and family members to reduce decision time in combination with the remote, telephonic cardiac resuscitative device to be discussed in detail herein, will provide safe, inexpensive and practical resuscitative coronary care within the brief length of time required in order to substantially increase the salvage rate of cardiac arrests occurring outside the hospital.

Prior art cardiac resuscitation or warning devices have, accordingly, generally been designed for use by mobile cardiac care units wherein a trained cardiac care team may defibrillate the patient with the aid of a portable defibrillator under the direction of a medical doctor. In U.S. Pat. No. 3,703,900, for example, a portable defibrillating apparatus is described wherein a U-shaped electrode current applicator with a handle and three electrodes may be applied to a patient which will sense for the presence of a normal heartbeat, indicate a poor contact, and, on command, activate a defibrillating device.

Alternatively, various prior art devices have been proposed for continuously monitoring a patient either in a hospital cardiac care unit or elsewhere for the purpose of determining the occurance of arrhythmias, cardiac arrest, etc. One such approach is illustrated in U.S. Pat. No. 3,724,455 wherein radio telemetry is employed to continuously monitor the EKG wave form which is recorded and/or which is analyzed to provide an alarm or otherwise signal to the patient what medication should be administered or what other action should be taken. In one embodiment, a signal may be transmitted by radio telemetry to activate, for example, a defibrillator which can be triggered by a central facility upon detection of ventricular fibrillation. Unfortunately, not only must the wearer maintain good electrode contact at all times, but should that contact be impaired or should the radio telemetry signal be interfered with, as for example, by entering large buildings constructed of steel or concrete, the quality of the signal transmitted by the device may mimic fibrillation or cardiac arrest, at which time the activation of the defibrillating device could cause the death of the wearer.

Alternatively, in U.S. Pat. No. 3,144,019 a cardiac monitoring device is disclosed for automatically monitoring a wide variety of cardiac arrhythmias or abnormalities and for automatically effecting electro-cardiographic recording thereof and for initiating and terminating appropriate treatment in response thereto. The device which is described therein is primarily intended for periods of prolonged observation especially necessary during cardiac surgical procedures and during a normal two day recuperating period after such operation during which time an arrhythmia is frequently the source of death. Upon sensing an arrhythmia, this apparatus is designed to automatically administer electric shock and/or to open the valves of drug circuits which are connected to a previously inserted IV.

While various other remote stimulators or injectors, such as those illustrated in U.S. Pat. No. 3,179,890 or 3,841,328 are known to the art of medical electronics, no practical device has yet been developed exhibiting adequate safeguards for the patient while at the same time delivering primary cardiac care within the length of time required in order to substantially increase the salvage rate of patients experiencing the onset of acute cardiac symptoms.

SUMMARY OF THE INVENTION

The present invention provides an extremely safe and reliable apparatus for treating patients beginning almost immediately at the onset of acute symptoms. Each patient with a history of cardiac symptoms, and various other public facilities such as theaters, sporting arenas, etc. are provided with patient operatable apparatuses which, in the preferred embodiment, are located in false bottom briefcases which are otherwise suitable for conventional business use. Disposed within these briefcases and normally concealed until needed for use, are various components which may be applied by the patient for the purpose of diagnosing and treating acute cardiac symptoms. In the preferred embodiment, these components include an electrode belt, a remote drug injector and a pulse monitor, each of which may be conveniently applied by the patient in a matter of less than one minute. Of these components, only the electrode belt need be applied in cases of dire emergency.

In the preferred embodiment, the electrode belt comprises a number of electrodes for sensing the electrocardiogram, testing the electrode contact, and defibrillating the patient, and at least a microphone for receiving voice communication from the patient and preferably also a strain gauge to sense the patient's respiratory rate.

In order to maintain a high degree of audio fidelity while at the same time utilizing standard telephone lines, which carry relatively narrow frequency ranges, the portable apparatus of the present invention further comprises a tone decoder and a number of relays so that only one diagnostic indicia is transmitted, in addition to voice communication, at any one time. Accordingly, in response to selections made by the physician, the physician may receive data concerning the state of the defibrillator charge in the patient's apparatus, the patient's pulse, the patient's respiration, or the quality of the patient-electrode contact. Where maximum data quality is preferred, the physician may additionally temporarily block the patient's voice input to the device so that that input can not interfere with data collection, as described above. In the preferred embodiment, the physician may continuously monitor the patient's condition and when needed, treat the patient by providing various degress of defibrillating charges and/or by injecting various amounts of any one of a plurality of drugs into the patient.

Various safety features are provided which monitor the performance of the device and the patient-physician interchange so that important data may be preserved for later study.

The physician operated module of the present apparatus in the preferred embodiment further comprises an automatic sequencer, which regulates the sequence in which commands can be given, will preferably automatically scan the vital signs of the patient to continuously update those signs and which sequencer coacts with a display decoder and command sequence display for indicating to the physician the latest physiologic data available as well as the command sequence which may be requested in order to perform any given treatment.

Accordingly, one of the primary objects of the present invention is the provision of a portable patient operatable apparatus which can aid a remote physician to diagnose and treat acute cardiac symptoms. A further object of the present invention is the provision of a physician operated apparatus which will monitor and command the aforementioned patient operatable apparatus to provide safe and reliable treatment to a remotely located patient suffering acute cardiac symptoms.

A further object of the present invention is the provision of a portable apparatus which is easily concealed in a briefcase or similar hand carried item which may be easily applied by untrained personnel in the event of an emergency, or by the patient alone at the onset of acute cardiac symptoms (i.e., chest pain).

A further aim of the present invention is the provision of an MD-operated apparatus wherein a sequencer permits the transmission of various treatment commands only in the presence of certain diagionstic conditions. A further object of the present invention is the provision of a novel remote drug injector. Another aim of the present invention is the provision of a safe, inexpensive and reliable telephonic cardiac resuscitation apparatus, the construction and circuitry of which possesses unique advantages over prior art devices.

These and other objects of the present invention will become apparent from the following more detailed description.

DETAILED DESCRIPTION OF THE DRAWINGS

Figure 1:
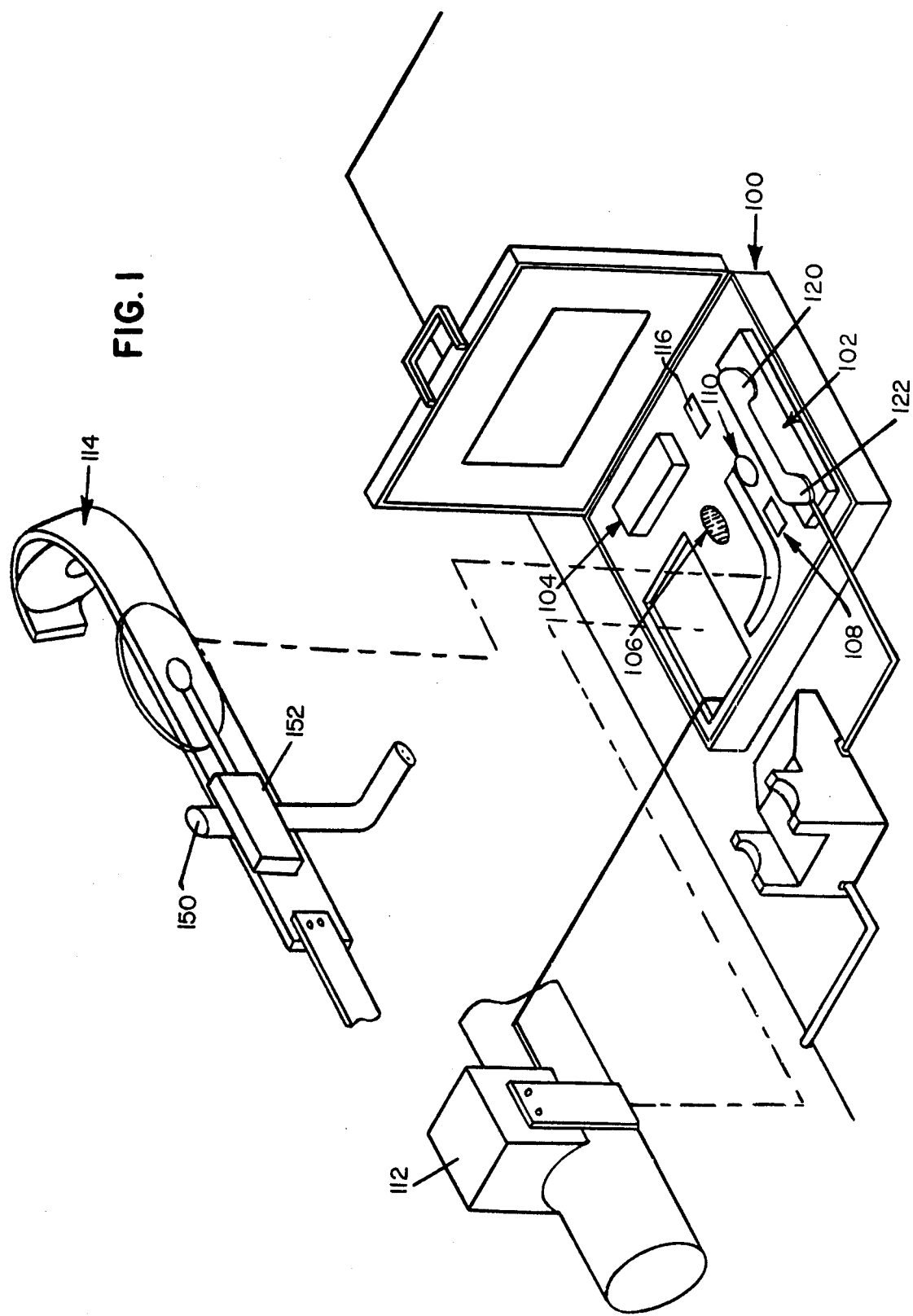
FIG. 1 is a diagramatic perspective view of the preferred embodiment patient operatable portion of the device of the present invention showing a false bottom briefcase wherein the patient operatable portion has been exposed to show the relative positioning of the preferred embodiment components within the briefcase; wherein the electrode belt and drug injector are shown exploded away from their storage positions in the case, the injector being shown attached around a portion of a patient's limb; and finally wherein a telephone is illustrated having its hand set positioned in the preferred embodiment audio transducer.

Although specific forms of the invention have been selected for illustration in the drawings, and the following description is drawn in specific terms for the purpose of describing these forms of the invention, this description is not intended to limit the scope of the invention which is defined in the appended claims.

Since in the vast majority of instances cardiac symptoms of an acute nature first occur while the patient is at home, at work, or travelling to or from work, the preferred embodiment of the present invention comprises a briefcase, which, in addition to functioning in a standard manner, has concealed therein a number of components which, through a telephone interface may be used to administer cardiac treatment beginning immediately at the onset of acute symptoms. As shown in FIG. 1, which is a representative layout of the components required in such a briefcase, the briefcase designated generally 100 has located therein a telephone transceiver designated generally 102, a battery defibrillator designated generally 104, a speaker designated generally 106, a battery charging receptacle designated generally 108 and a low voltage warning device designated generally 110. In the preferred embodiment, a battery charger is not incorporated in the briefcase due to the additional weight which would be required in order to include that incorporation. In alternate embodiments, either a transformer suitable to plug into line voltage or the charger itself may be incorporated in the briefcase provided a degree of miniaturization can be achieved so that the overall weight of the briefcase is not excessive. Fitted into pockets formed in the briefcase are drug injector 112 and an electrode belt designated generally 114 each of which will be described more fully in connection with FIGS. 5 and 2 respectively. A pulse detector 116 which is preferably of the photoelectric finger encapsulating type is similarly fitted into a pocket and the electrode belt 114, drug injector 112, and pulse detector 116 are each mounted for quick removal for application to the patient upon the occurance of acute cardiac symptoms. The remainder of the electronic circuitry disclosed in FIG. 3, may be suitably concealed in any convenient location within the briefcase and is not specifically illustrated in FIG. 1.

It may be seen from FIG. 1 that upon experiencing symptoms, such as chest pains, all of the components applied to the patient are readily accessible. Since, in most instances the onset of acute symptoms will be witnessed and further since cardiac arrest, fibrillation, and/or serious arrhythmias are not likely to occur for several minutes, it is not anticipated that any serious difficulty should be encountered in establishing physician contact and applying the required peripheral equipment to the patient in time to render meaningful medical assistance. In one embodiment of the present invention a miniaturized pre-programed automatic dialer is incorporated as part of the telephone transceiver designated generally 102 so that in order to establish physician contact the hand set need merely be dropped into the telephone transceiver into receiving cups 120 and 122 and the dialer activated to establish physician contact. As will be described hereinafter, the physician's voice will be transmitted to the patient at all times through the speaker designated generally 106 and the patient may respond to the doctor using microphone 150 which is mounted on chassis 152 of the electrode belt.

By utilizing an automatic dialer, the patient is forced to remove the electrode belt designated generally 114 immediately whereupon the belt will be applied around the chest so that the microphone 150 is in the position of a lapel microphone for subsequent communication with the physician. Following application of the electrode belt designated generally 114 to the patient, the physician may then direct the patient to apply the drug injector 112 or pulse indicator 116 of conditions permit. In any event, these three components remain linked to the remaining portion of the apparatus at all times by flexible cords such as telephone cords which allow the patient relatively free movement during the subsequent treatment process.

Figure 2:
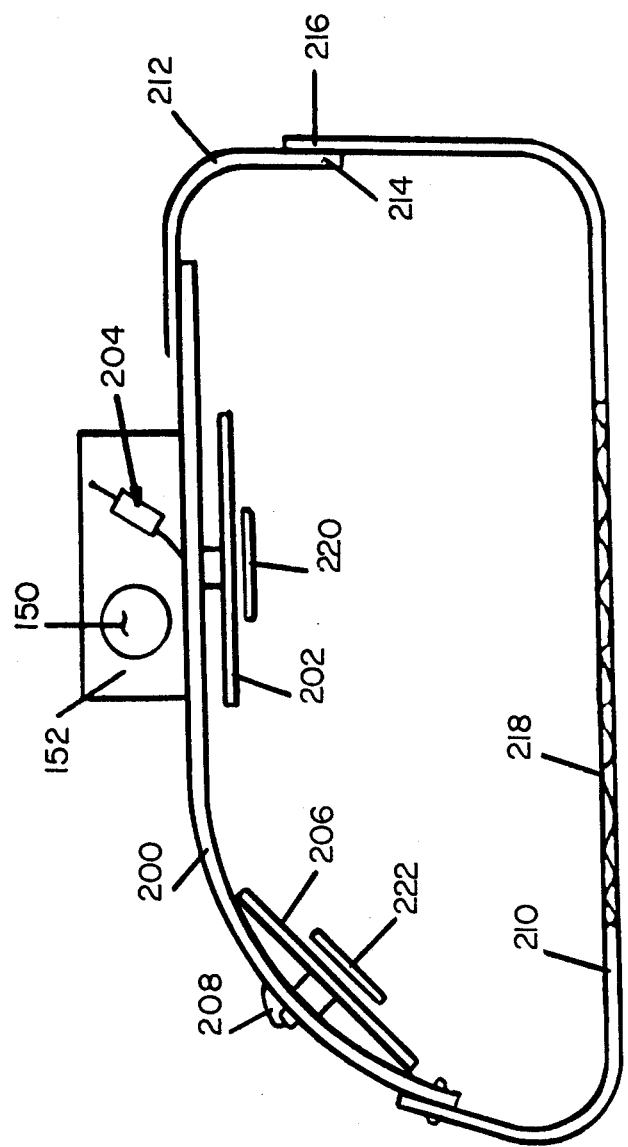
FIG. 2 is a diagrammatic top view of the preferred embodiment electrode belt of the present invention.

Referring to FIG. 2 the particular preferred construction of the electrode belt is illustrated. The main relatively rigid body 200 of the electrode belt is preferably constructed of an insulating material such as Plexiglass in a position which will be located in a $V_1$-$V_5$ position over the heart. A cardiac electrode 202 is oriented on a first side of the electrode belt body 200. On the opposite side of the body 200 from electrode 202 is mounted chassis 152 which has the above-mentioned microphone 150 mounted thereon as well as a strain gauge designated generally 204 which is adapted to sense the periodic strain which is produced on electrode 202 by the patient's respiration. A second electrode 206 is provided as shown in FIG. 2 off to one side of the second electrode to engage the corner of the rib cage. The lead 208 from this electrode is illustrated running generally along the outer surface of the body 200 of the electrode belt to the chassis 152 where the main connection to the briefcase will be made. A flexible or velcro strap 210 is attached to one end of the body 200 while at the other end of the body 200 a second buckling portion 212 is shown which, if made of velcro will quickly attach at its tip 214 to the overlapping tip 216 of strap 210. Woven or otherwise disposed so that it will make contact with the back of the patient is a grounding wire 218 which also runs to chassis 152, the function of which grounding wire will be discussed more fully hereinafter.

Since it is important that excellent contact be produced by the electrodes 202 and 206 upon application of the electrode belt to the patient, it may be seen that by disposing the electrodes 202 and 206 adjacent the interior surface of a generally concave portion of the rigid body 200 of the electrode belt, that once that belt is firmly applied to the patient, contact will be maintained regardless of the patient's size, the particular body dimensions, or the precise location of the belt on the body. The plastic body 200 of the electrode belt may accordingly, be heated and molded to exactly fit the user's body. In order to assure a good electrical contact, paste applicators 220 and 222 are disposed on electrodes 202 and 206 respectively, which paste applicators will automatically rupture or otherwise apply paste across the surfaces of the electrodes 202 and 206 between the outer surfaces thereof and the body of the wearer.

Figure 5:
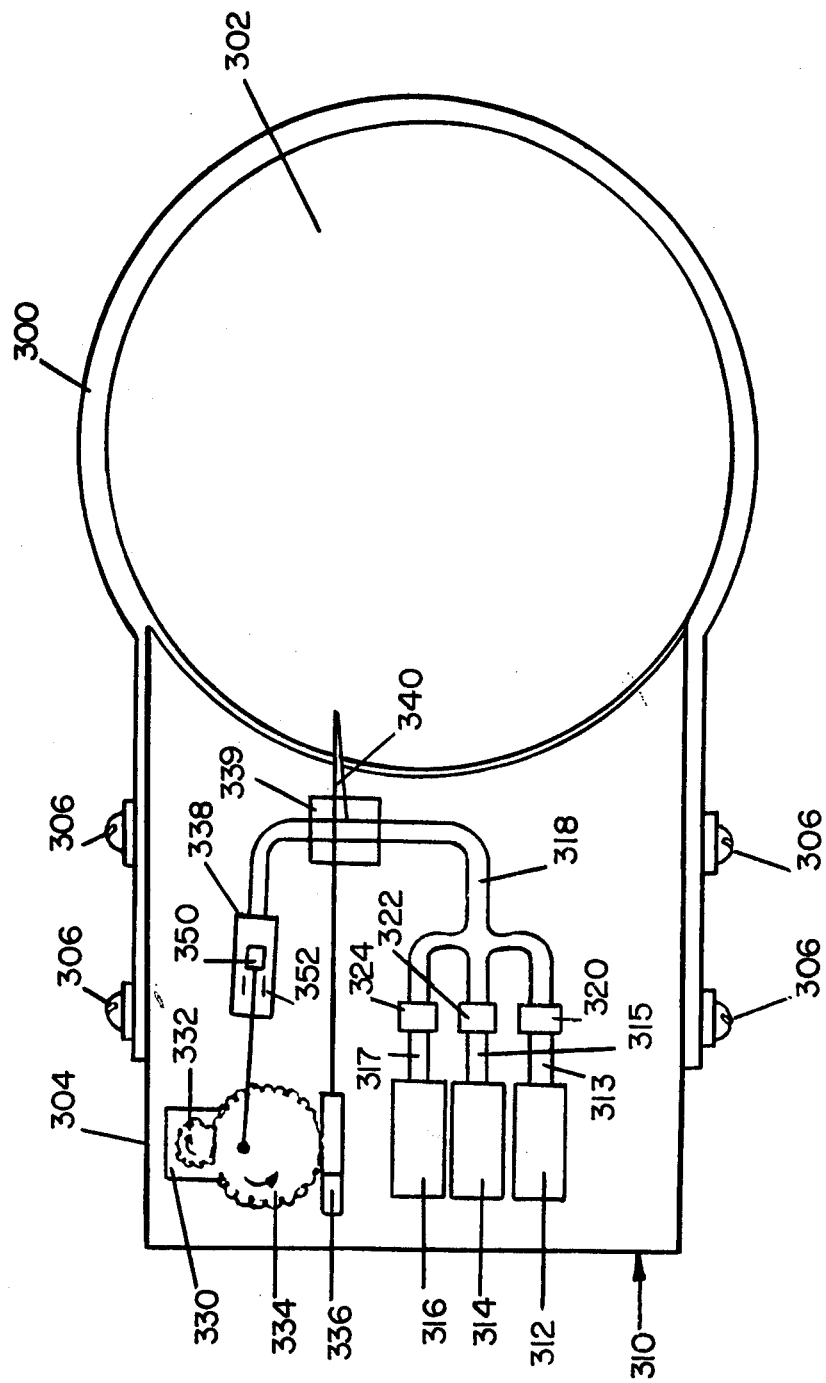
FIG. 5 is a diagrammatic cross-section of the preferred embodiment drug injector of the present invention shown attached to a patient's limb with a needle in its extended position.

Referring now to FIG. 5 wherein a diagrammatic cross-section of the drug injector is illustrated, a velco strap 300 has been applied around an arm or thigh of a patient 302 to strap drug injector chassis 304 thereagainst. The velcro strap 300 is conveniently fastened to the chassis by screws 306 or other suitable fastening means. Within the drug injector designated generally 310 are disposed three vials of different drugs 312, 314, and 316 respectively. Each of these vials is connected to a main conduit 318 via channels 313, 315, and 317 which are valved by solenoids 320, 322, and 324 which are selectively controlled by the physician, as will be described hereinafter. A small electric motor 330 is mounted in one corner of the chassis 304 as shown. The drive gear 332 is adapted to mesh with syringe gear 334 which not only cooperates with rack 336 during the needle extension phase of drug injection, but also continuously cooperates with syringe piston 338 to draw pre-measured aliquots of any of the drugs indicated and then, by continuing the rotation shown by arrow A on gear 334, injecting that pre-measured aliquot through needle 340 intramuscularly into the patient.

The needle extension process accordingly functions as follows: when the drug injector is initially applied to the arm or thigh of the patient, the needle 340 is fully withdrawn within the chassis 304 and the rack 336 is in the phantom position shown in FIG. 5. When the motor 330 is activated to cause the rotation of gear 332 in the direction shown to cause rotation of gear 334 in the direction of arrow A, will cause the rack to extend the needle 340 until the gear has reached its full extent of travel. If desired, the motor may be a reversible motor which, following treatment, may be withdrawn upon the physician's command. In addition to extending the needle 340, the rotation of gear 334 will pull syringe plunger 350 along syringe channel 352 so that which ever solenoid valve of valves 320, 322, and/or 324 are open, a preselected aliquot of the particular drug controlled thereby will be pulled into main conduit 318. Since each solenoid valve is a single direction flow control valve, and further since "T" connection 339 is a flow control valve, as the gear 334 continues around so that the syringe plunger 350 begins to move in the opposite direction, the drug will be injected into the arm of the patient. When injection is complete, after a full rotation of the gear 334, the motor automatically shuts off awaiting its next command. Accordingly, each command received from the physician will result in the injection of a preselected aliquot of a particular drug and, if desired, successive commands can inject successive aliquots of different drugs such as lidocaine, morphine, etc. into the patient in order to alleviate particular symptoms. Although for purposes of illustration the main conduit 318 and other supply channels have been illustrated having a relatively large cross-section, in practice the syringe 338 and more particularly the syringe channel 352 and piston 350 therein will comprise the only significant volume between drug vials 312, 314, and 316 and the needle 340. Accordingly, "crosstalk" between injections of different drugs will not present a significant problem.

Figure 3:
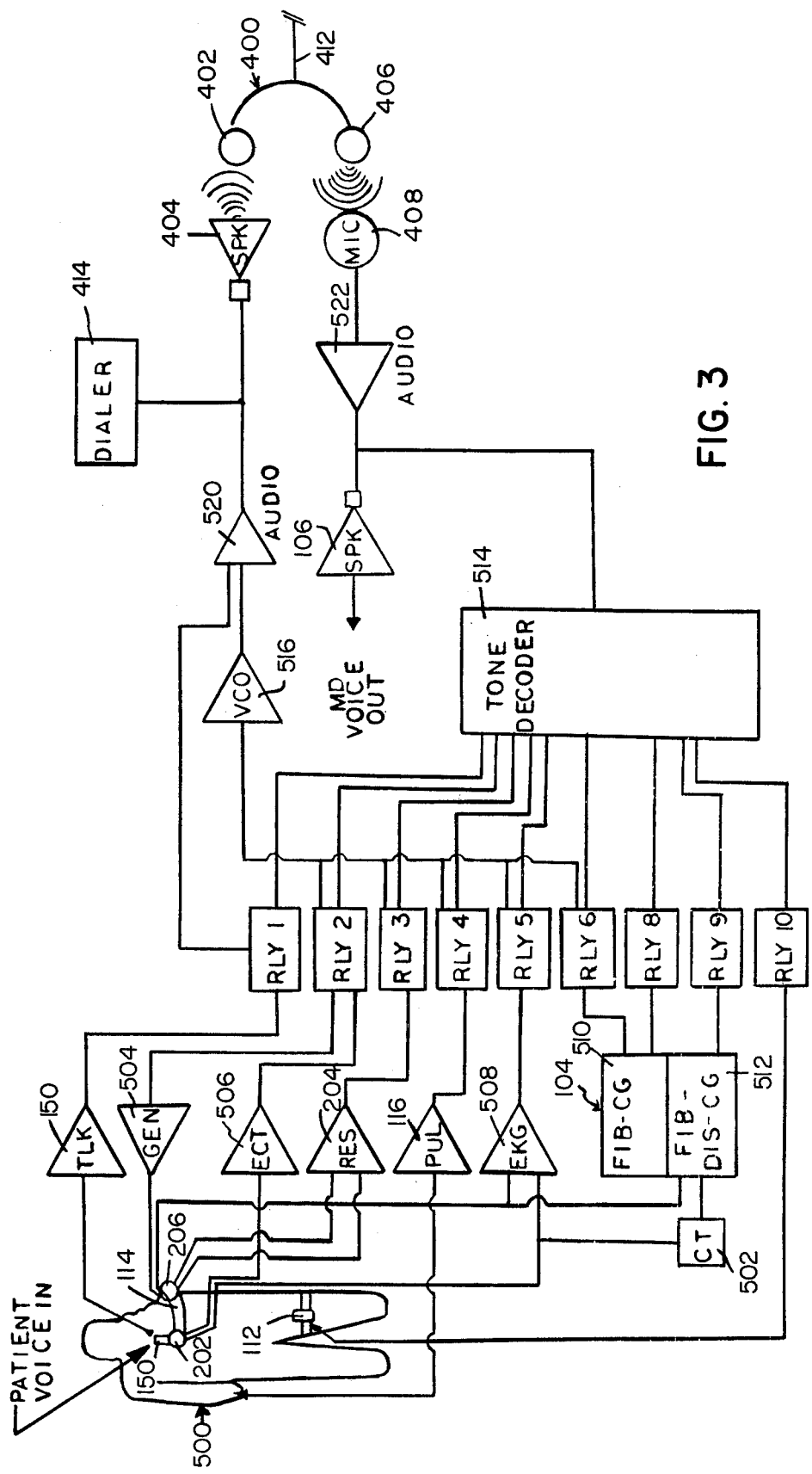
FIG. 3 is a block diagram of the patient operatable portion of the preferred embodiment apparatus of the present invention.

Referring now to FIG. 3 the operation and interrelationship of the various components included in the patient's portion of the device of the present invention is clearly illustrated. The hand set designated generally 400 of the telephone is shown with its associated cord 412. The microphone portion 402 thereof is located generally adjacent the speaker 404 of the telephone transceiver 102 in FIG. 1. Similarly, the speaker portion 406 of the telephone hand set 400 is located adjacent a microphone 408 of that transceiver. In accordance with the preferred embodiment of the present invention once physician contact has been established preferably by dialer 414, the physician will be in a position to transmit various coded tones through speaker 406 into microphone 408 for the purpose of controlling data which is fed back through speaker 404 as well as in controlling the various treatment modes such as defibrillation and drug injection, as discussed above.

The various functions performed with respect to the patient designated generally 500 are illustrated by the triangular blocks near the left of FIG. 3 which are labelled with three letter designations, with the exception of the defibrillator designated generally 104 and the counter 502 which are located near the bottom left of that figure. Accordingly, the triangular block labelled "TLK" and numbered 150 indicates the ability of microphone 150 attached to electrode belt 114 to transmit the patient's voice to the remainder of the apparatus. Similarly, triangular blocks 504 and 506 labelled "GEN" and "ECT" which comprise the electrode contact test circuit, as will be described more fully hereinafter, are illustrated in FIG. 3. Block 204 labelled "RES" refers to respiration, block 116 labelled "PUL" refers to pulse and block 508 labelled "EKG" referring to the sensing of the patient's electrocardiogram. The defibrillator designated generally 104 is illustrated having two stages, a first defibrillator charging circuit 510 and the defibrillator discharge circuit 512, the discharge of which is counted by counter 502 for the purposes of later study. Of the various functions discussed above, the physician may selectively control whether or not the state of defibrillator charge, the electrocardiogram, the pulse, the respiration, the quality of electrode contact, or the voice is transmitted in some form as information to speaker 404 for relay to the physician. For the functions illustrated in FIG. 3 this is accomplished using six relays as illustrated in the blocks labelled "RLY" numbered 1 to 6 and shown under the control of tone decoder 514. The remaining relays, relay 8, 9, and 10 shown in FIG. 3, which are also under the control of the tone decoder 514 activate the treatment circuits, namely the charging of the defibrillator through defibrillator charging circuit 510, the discharging of the defibrillator 512 and the activation of the drug injector 112. While for purposes of convenience a single relay, relay 10 is shown associated with drug injector 112, it is understood that at least one relay will be required for each drug to be injected, and, if preferred an additional relay or plurality of relays to control the motor of the drug injector, as desired.

Due to the limited band width of the telephone, it is not feasible to maintain good data collection and analysis while collecting information simultaneously from more than one source. It is possible to a certain extent, however, due to the discontinuous nature of voice communication, to leave open the talk circuit 150 while other information is being transmitted to speaker 404. Additionally, since a voltage control oscillator 516 is utilized to convert all data collected other than voice transmission into a varying pitch, it has been found that it is possible to talk over that pitch, while interfering minimally with voice communication. Accordingly, as shown in FIG. 3, relay 1 which is, nonetheless, operable by the tone decoder will normally transmit information from microphone 150 to audio amplifier 520 to speaker 404 for transmission to the physician. In the event that the patient becomes hysterical, and/or in the event that the physician wishes to confirm the fact that the voice transmission is not interfering with the physiologic data otherwise collected by the device, activation of relay 1 will serve to cut off the microphone 150 and allow only that other data which is then being collected to be transmitted to speaker 404.

Figure 4:
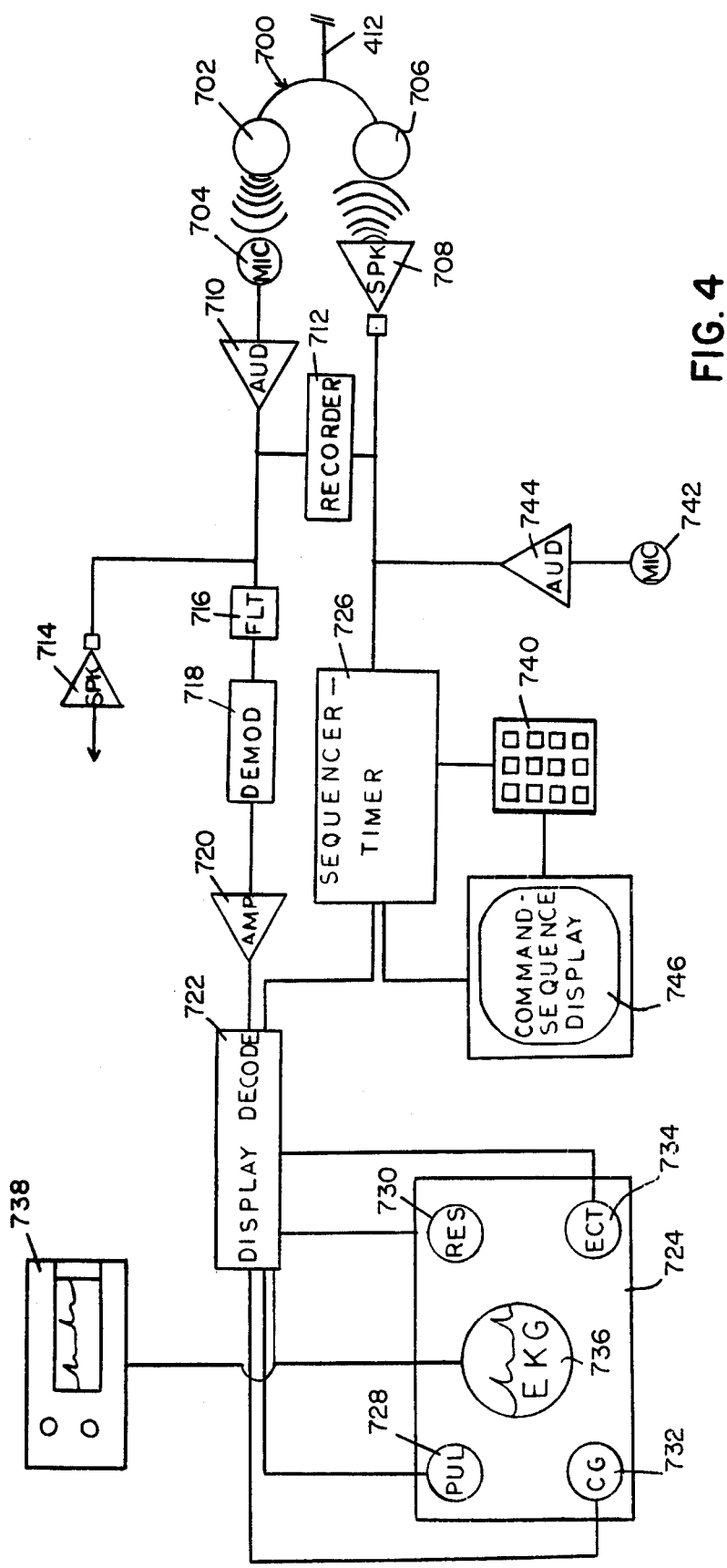
FIG. 4 is a block diagram of the physician operated portion of the preferred embodiment apparatus of the present invention.

Of the remaining relays 2 through 6, it is anticipated that only one of such relays may be in the "on" position at any one time. As will be discussed hereinafter, a sequencer in the physician's portion of the apparatus will sequentially provide tones to the tone decoder 514 so that the physiologic data collected from the sensing circuits, particularly the EKG will be continuously updated, while discharge of the defibrillator will be prevented prior to the provision of a particular specified command sequence to insure the safety of the patient. In all events, the physician's voice as amplified through audio amplifier 522 will be emitted from speaker 106 located in the attache or briefcase so that verbal instructions may always be provided to the patient and/or bystanders. Referring now to FIG. 4 which illustrates the physician's portion of the device, the physician's hand set designated generally 700 with telephonic line 412 attached thereto is illustrated wherein the speaker portion of the hand set 702 is located generally adjacent the physician's telephone transceiver, and more particularly the microphone 704 thereof. Similarly, the microphone portion 706 of the hand set 700 is disposed adjacent the speaker 708 of the physician's portion of the apparatus to receive verbal and coded tone commands therefrom. A conventional audio amplifier 710 is disposed to amplify signals received from the microphone and the recorder 712 records the entire interchange between the patient and physician for legal as well as study purposes. A speaker 714 is connected to the audio amplifier so that whatever audio signal, whether voice or frequency modulation, is received from the hand set will be broadcast to the physician. Depending upon the band width of the voltage control oscillator 516 selected for use in the patient's device, a filter 716 will eliminate any static and preferably a portion of the voice so that, as far as practical, only the output of the voltage control oscillator will be transmitted for demodulation by the demodulator 718. The output of the demodulator 718 is amplified by a conventional amplifier 720 and fed to the display decoder 722 which acts to route the demodulated information to the particular display on display board 724. The display decoder is capable of routing the information received from the demodulator 718 as a result of its cooperation with the sequencer-timer 726, which in addition to transmitting coded tone commands to the patient's portion of the apparatus, similarly signals the display decoder so that the decoder is capable of recognizing the type of information which is then received from the patient's portion of the apparatus. Accordingly, for purposes of illustration various cathode ray-type display devices 728 for pulse, 730 for respiration, 732 for the state of defibrillator charge and 734 for the quality of the electrode contact are illustrated, while the primary electrocardiogram display 736 is illustrated both as a transient cathode ray display 736 and as a fixed chart recorded electrocardiograph through chart recorder 738.

In accordance with the preferred embodiment of the present device, the physician is capable of selecting at will the particular physiologic data in which he is interested by punching suitable commands on a tone pad 740. The physician is also in continuous contact with the patient through microphone 742, the output of which is amplified by audio amplifier 744 prior to transmission to speaker 708. In the preferred embodiment the command sequence display 746 is also provided not only to provide a visual indication to the physician of the particular commands which have been given, and accordingly, the mode of information which is being detected, but also for the purpose of indicating to the physician information concerning the sequence of commands which are required in order to accomplish certain treatments, such as defibrillation, while additionally providing a running record of the amount and/or number of treatments, such as drug injections, which have already been applied.

In practice the operation of the preferred embodiment device proceeds as follows: after application of the drug injector 112, pulse detector 116 and electrode belt 114 by the patient, as described above, the physician may, by punching the appropriate code on tone pad 740 select any particular item of physiologic data in which he has an interest in order to obtain an immediate display of that information. In most instances, however, the physician may be preoccupied by speaking to the patient and attempting to direct the patient into a particular position etc. which is most favorable for him under the circumstances. In this instance, the sequencer-timer is pre-programmed to sequence through either a brief or extended scan to ascertain each of the physiologic references to be ascertained by the device and to update the display of those references on the display panel 724. During the initial phases of the consultation between patient and doctor, a full scan of the quality of electrode contact, respiration, pulse and electrocardiogram should be feasible and preferred. During the latter stages of treatment, in the event that the symptoms become more acute, it is anticipated that the pulse and respiration will be eliminated from the brief scan and defibrillator charge state will be substituted therefore. The reason for this substitution is the fact that, due to respiration and pulse rates requiring significant lengths of time in order to accurately determine same, during critical phases of treatment it will not be desired to tie up the non-voice communication channel in order to collect such data in favor of the remaining data. At least the electrode contact test circuit and fibrillator charge state data may be collected relatively quickly, leaving the bulk of the transmission time free for continuously monitoring the electrocardiogram. Since lidocaine, the most commonly administered drug, takes approximately ten minutes, when intramuscularly injected, to reach satisfactory blood levels, in most instances the physician will apply this drug relatively early during the treatment process. In one embodiment of the present invention, the timer 726 which is a part of the sequencer-timer apparatus, may be used in order to regulate the administration of a drug such as lidocaine. Accordingly, the physician will select the particular drug by punching in the appropriate signal therefore on tone pad 740 and will select the number of units of that drug to be administered, which units will be regulated by timer 726 which controls the numbered of revolutions of gear 322 and the amount of drug injected. The command sequence display in all instances will keep a cumulative record of the amount of lidocaine or other drugs actually injected into the patient, and, if preferred, will clock the time of injection so that the physician will know approximately how many minutes it has been since a given unit dosage of that drug has been injected so that he can determine whether sufficient time has elapsed for optimal blood levels to have been reached.

The most crucial time during the operation of any cardiac resuscitation device is the occurence of cardiac fibrillation, during which the appropriate discharge from a defibrillator may restart a regular heartbeat, thereby saving a patient who would otherwise die. Once fibrillation or a similar condition occurs, it is desired that the administration of a shock not be given for a number of seconds during which time the patient should lose consciousness, and thereby not feel the pain which would otherwise be associated with the administration of such a shock. Accordingly, when the EKG display indicates that fibrillation is taking place, the physician may press the defibrillation sequence wherein the defibrillator charging circuit, relay 8, is activated to begin to charge the defibrillator, the electrocardiogram updated, the electrode contact test circuit activated to insure adequate contact between the electrodes and the patient such that administration of a defibrillating shock will not cause a burn, and finally display of the degree of defibrillation charge which will be administered by the physician upon the "go" command which activates relay 9. In the event that a qrs signal is received by the EKG, the electrode contact test circuit indicates insufficient contact or the defibrillator charge indicates insufficient charge, the sequencer-timer will automatically display substandard data and block defibrillation commands. The physician may take steps to correct the deficiency, as for example by directing bystanders or witnesses to readjust the electrode belt to establish a better electrode contact, whereupon the defibrillation sequence may be restarted. Upon completion of a satisfactory defibrillation sequence, the physician may command defibrillation by pressing a conventional defibrillation command into tone pad 740. Alternatively, if conditions do not permit the correction of a deficiency, the physician may, when necessary, press a defibrillation override command. In the event the patient is not resuscitated, the procedure may be repeated, hopefully until resuscitation is accomplished. Since each of the commands, the voice contact and all of the data collected from the patient is recorded by recorder 712, a record will be generated which, for teaching purposes or otherwise, is capable of recreating the entire sequence of treatment, and will be available to the physician as a part of the patient's file for use, for example, in preparing for further consultations with the patient.

As a result, it may be seen that a safe, efficient, reliable device is provided wherein state of the art care is delivered to a patient experiencing acute cardiac symptoms, and that, particularly where the onset of those symptoms is witnessed, a physician or trained cardiologist can administer care heretofore available only through mobile cardiac care units responding to promptly lodged calls for assistance.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. A remote, telephonic, cardiac resuscitation apparatus comprising a portable, patient-operatable portion and a remote physician-operatable portion; said patient operatable portion comprising:
    (a) an acoustic telephone coupler;
    (b) means associated with said coupler for treating said patient in response to coded tones received through said coupler;
    (c) means for sensing a plurality of types of physiologic data indicating the cardiologic condition of said patient and for coding said data as a coded tone; and
    (d) means responsive to a coded tone received from said acoustic coupler for selectively transmitting no more than one type of said coded data to said audio coupler.

2. The invention of claim 1 wherein said patient-operatable portion further comprises means for selectively, simultaneously transmitting the patient's voice to said coupler.

3. The invention of claim 1 wherein said types of physiologic data further comprise the patient's electrocardiogram.

4. The invention of claim 3 wherein said types of physiologic data comprise the patient's pulse rate.

5. The invention of claim 3 wherein said types of physiologic data comprise the quality of defibrillator electrode contact with said patient.

6. The invention of claim 3 wherein said types of physiologic data further comprise the patient's respiration rate.

7. The invention of claim 1 wherein said means associated with said coupler for treating said patient further comprises a defibrillator, and wherein said apparatus further comprises means for determining the operative state of said defibrillator with respect to said patient.

8. The invention of claim 7 wherein said apparatus further comprises means responsive to a coded tone received by said acoustic coupler for selectively transmitting to said coupler information reflecting said determination of the operability of said defibrillator.

9. The invention of claim 8 wherein said operability of said defibrillator is determined by means for sensing the degree of charge of said defibrillator.

10. The invention of claim 8 wherein the state of operability of said defibrillator is determined by means for sensing the quality of electrode contact with said patient.

11. The invention of claim 1 wherein each of said types of data collected by said apparatus is selectively coded by a voltage control oscillator into a single variable pitch.

12. The invention of claim 1 wherein said means for treating said patient comprises a drug injection.

13. The invention of claim 12 wherein said injection selectively injects predetermined aliquots of any of a plurality of drugs.

14. The invention of claim 13 wherein said injector comprises a syringe, means for reciprocating said syringe, a plurality of drug reservoirs, each selectively communicable through a conduit with said syringe, and a needle communicating with said conduit.

15. The invention of claim 14 wherein said means for reciprocating further comprises means for extending said needle into said patient.

16. The invention of claim 15 wherein said selective communication is through a single direction solenoid controlled valve.

17. The invention of claim 1 wherein said patient operatable portion further comprises a briefcase, said remainder of said apparatus portion being disposed below a false bottom thereof.

18. A remote, telephonic, cardiac resuscitation apparatus comprising a portable, patient-operatable portion and a remote physician-operatable portion, said physician operatable portion comprising:
    (a) an acoustic telephone coupler;
    (b) means for decoding physiological data received in the form of a variable pitch from said acoustic coupler;
    (c) means for displaying said data to said physician; and
    (d) means for transmitting coded tones to said acoustic coupler for selecting the physiologic data to be collected by said patient operatable portion, and for providing commands to said patient operatable portion to treat said patient.

19. The invention of claim 18 wherein said apparatus further comprises means for maintaining verbal communication between said physician to said patient during said transmission.

20. The invention of claim 18 wherein said apparatus further comprises means for selectively preventing verbal communication from said patient to said physician at least during said transmission of said physiologic data.

21. The invention of claim 18 wherein said apparatus further comprises sequencing means associated with said means for transmitting coded tones, said sequencing means cooperating with said decoding means to periodically collect and selectively display at least said physiologic data through said physician-operatable portion.

22. The invention of claim 21 wherein said sequencer controls the sequence with which particular coded tone commands will be transmitted to said acoustic coupler.

23. The invention of claim 22 wherein said apparatus further comprises a command sequence display associated with said sequencer for indicating the required command sequence.

24. The invention of claim 23 wherein said apparatus further comprises a timer, whereby the duration of a specific operation performed by said patient operatable apparatus may be selected by said physician.

* * * * *